US 7,285,576 B2
Oct. 23, 2007

(12) United States Patent
Hyde et al.

(10) Patent No.: US 7,285,576 B2
(45) Date of Patent: Oct. 23, 2007

(54) ABSORBENT POLYMER COMPOSITIONS, MEDICAL ARTICLES, AND METHODS

(75) Inventors: Patrick D. Hyde, Burnsville, MN (US); Robert H. Menzies, Waupaca, WI (US)

(73) Assignee: 3M Innovative Properties Co., St. Paul, MN (US)

( * ) Notice: Subject to any disclaimer, the term of this patent is extended or adjusted under 35 U.S.C. 154(b) by 686 days.

(21) Appl. No.: 10/387,236

(22) Filed: Mar. 12, 2003

(65) Prior Publication Data
US 2006/0173087 A1   Aug. 3, 2006

(51) Int. Cl.
*C08J 9/36* (2006.01)
(52) U.S. Cl. .................. 521/50; 424/489; 604/378; 604/379
(58) Field of Classification Search ............ 424/489; 521/50; 604/378, 379
See application file for complete search history.

(56) References Cited

U.S. PATENT DOCUMENTS

| | | | |
|---|---|---|---|
| 2,521,713 A | 9/1950 | Goetz | 167/14 |
| 2,736,721 A | 2/1956 | Dexter | 260/42 |
| 3,685,993 A | 8/1972 | Mukherjee | 96/33 |
| 3,761,590 A | 9/1973 | Fox, Jr. | |
| 3,800,792 A | 4/1974 | McKnight et al. | 128/156 |
| 3,841,953 A | 10/1974 | Lohkamp et al. | 161/150 |
| 3,911,115 A | 10/1975 | Hadhanyi | 424/180 |
| 4,024,312 A | 5/1977 | Korpman | 428/343 |
| 4,340,043 A | 7/1982 | Seymour | 128/132 |
| 4,528,321 A | 7/1985 | Allen et al. | 524/761 |
| 4,590,227 A | 5/1986 | Nakamura et al. | 523/130 |
| 4,603,152 A | 7/1986 | Laurin et al. | 604/265 |
| 4,646,730 A | 3/1987 | Schonfeld et al. | 728/156 |
| 4,652,465 A | 3/1987 | Koto et al. | 427/216 |
| 4,728,323 A | 3/1988 | Matson | |
| 4,892,528 A | 1/1990 | Suzuki et al. | 604/385 |
| 4,921,704 A | 5/1990 | Fabo | 424/446 |
| 5,075,373 A | 12/1991 | Takemori et al. | 525/57 |
| 5,176,952 A | 1/1993 | Joseph et al. | 428/284 |
| 5,209,971 A | 5/1993 | Babu et al. | 428/343 |
| 5,214,119 A | 5/1993 | Lehr et al. | 528/28 |
| 5,270,358 A | 12/1993 | Asmus | 524/55 |
| 5,326,567 A | 7/1994 | Capelli | 424/405 |
| 5,340,363 A | 8/1994 | Fabo | 604/304 |
| 5,369,155 A | 11/1994 | Asmus | 524/55 |
| 5,389,092 A | 2/1995 | Guillemet et al. | 604/304 |
| 5,409,472 A | 4/1995 | Rawlings et al. | 604/307 |
| 5,418,257 A | 5/1995 | Weisman | 521/54 |
| 5,429,819 A | 7/1995 | Oka et al. | 424/400 |
| 5,432,000 A * | 7/1995 | Young et al. | 428/372 |
| 5,437,932 A | 8/1995 | Ali et al. | 428/461 |
| 5,454,886 A | 10/1995 | Burrell et al. | |
| 5,476,712 A | 12/1995 | Hartman et al. | 428/317 |
| 5,512,041 A | 4/1996 | Bogart | 602/58 |
| 5,516,581 A | 5/1996 | Kreckel et al. | 428/317 |
| 5,567,779 A | 10/1996 | Sackmann et al. | 525/329 |
| 5,681,575 A | 10/1997 | Burrell et al. | |
| 5,681,579 A | 10/1997 | Freeman | 424/448 |
| 5,744,151 A | 4/1998 | Capelli | 424/405 |
| 5,750,134 A | 5/1998 | Scholz et al. | 424/434 |
| 5,844,013 A | 12/1998 | Kenndoff et al. | 521/137 |
| 5,848,995 A | 12/1998 | Walder | 604/265 |
| 6,039,940 A | 3/2000 | Perrault et al. | 424/78 |
| 6,103,152 A | 8/2000 | Gehlsen et al. | 264/45 |
| 6,126,931 A | 10/2000 | Sawan et al. | 424/78 |
| 6,130,303 A | 10/2000 | Neff et al. | 526/306 |
| 6,156,678 A | 12/2000 | Mukaida et al. | 442/118 |
| 6,201,164 B1 | 3/2001 | Wulff et al. | 602/48 |
| 6,270,792 B1 | 8/2001 | Guillemet et al. | 424/443 |
| 6,277,892 B1 | 8/2001 | Deckner et al. | 514/772 |
| 6,284,362 B1 | 9/2001 | Takai et al. | 428/326 |
| 6,288,076 B1 | 9/2001 | Kostyniak et al. | 514/299 |
| 6,297,335 B1 | 10/2001 | Funk et al. | 526/317 |
| 6,355,858 B1 | 3/2002 | Gibbins | 602/41 |
| 6,379,791 B1 | 4/2002 | Cernohous et al. | 428/355 |
| 6,436,420 B1 | 8/2002 | Antelman | |
| 6,458,877 B1 | 10/2002 | Ahmed et al. | 524/275 |
| 6,468,521 B1 | 10/2002 | Pedersen et al. | 424/78 |
| 6,548,727 B1 | 4/2003 | Swenson | 602/41 |
| 6,582,711 B1 | 6/2003 | Asmus et al. | 424/405 |
| 6,605,751 B1 | 8/2003 | Gibbins et al. | 602/41 |
| 6,797,743 B2 | 9/2004 | McDonald et al. | |
| 6,838,078 B2 | 1/2005 | Wang et al. | 424/78 |

(Continued)

FOREIGN PATENT DOCUMENTS

CN    1169883 C    10/2004

(Continued)

OTHER PUBLICATIONS

Gibbins et al.; Clinical study entitled "An In-Vitro Comparison of a New Antimicrobial Polyacrylate Absorbent Wound Dressing Containing Silver with the Silver-containing Antimicrobial Film Dressings" from AcryMed dated Oct. 1999 (7 pgs.) printed Sep. 27, 2001.
"Surgical Materials"; British Pharmacopoeia, 1993, Addendum 1996, pp. 1943-1944; HMSO London, England.
Calvert et al.; "Photochemistry"; Chapter II; John Wiley & Sons Inc. (1966) pp. 27-125.
Sheet entitled "Rheology Modifiers" from Ciba Specialty Chemicals 2001 (1 pg.).
Brochure entitled "Ciba® SALCARE® SC95—Rheology Modifier" from Ciba Specialty Chemicals 2001 (5 pgs.).
Tech Brief from NASA Tech Briefs entitled "Bayer Develops New Superabsorbent Polymers"; printed Oct. 2, 2001 (1 pg.).
Odian, G.; "Principles of Polymerization"; 3rd Edition; 1991; pp. Table of Contents and 352-353.

(Continued)

*Primary Examiner*—Terressa Boykin
(74) *Attorney, Agent, or Firm*—Ann Mueting (57) ABSTRACT

An absorbent polymer composition, which can be in the form of a foam, that includes a polymeric material, absorbent particles and thermally expandable (or expanded) microspheres.

34 Claims, 2 Drawing Sheets

U.S. PATENT DOCUMENTS

| | | |
|---|---|---|
| 2001/0010016 A1 | 7/2001 | Modak et al. ............... 623/42 |
| 2002/0156150 A1* | 10/2002 | Williams et al. ........... 523/113 |
| 2003/0021832 A1 | 1/2003 | Scherr ...................... 424/445 |
| 2003/0032765 A1 | 2/2003 | McDonald et al. |
| 2003/0049300 A1 | 3/2003 | Terry ........................ 424/423 |
| 2003/0118629 A1 | 6/2003 | Scholz et al. ............... 424/443 |
| 2003/0149106 A1 | 8/2003 | Mosbey et al. ............. 514/554 |
| 2003/0175503 A1 | 9/2003 | Lucast et al. ............... 428/343 |
| 2003/0185889 A1 | 10/2003 | Yan et al. .................. 424/484 |
| 2004/0180093 A1 | 9/2004 | Burton et al. ............... 424/489 |
| 2005/0025794 A1 | 2/2005 | Wang et al. ................ 424/401 |
| 2005/0123590 A1 | 6/2005 | Burton et al. |
| 2005/0123621 A1 | 6/2005 | Burton et al. |
| 2005/0124724 A1 | 6/2005 | Burton et al. |
| 2006/0034899 A1 | 2/2006 | Ylitalo et al. |
| 2006/0035039 A1 | 2/2006 | Ylitalo et al. |
| 2006/0233888 A1 | 10/2006 | Burton et al. |
| 2006/0233889 A1 | 10/2006 | Burton et al. |

FOREIGN PATENT DOCUMENTS

| | | |
|---|---|---|
| DE | 2 260 536 | 7/1974 |
| DE | 273 846 A1 | 11/1989 |
| DE | 199 58 697 A1 | 6/2001 |
| EP | 0 126 528 A2 | 11/1984 |
| EP | 0 172 025 B1 | 2/1986 |
| EP | 0 172 724 A2 | 2/1986 |
| EP | 0 326 382 B1 | 8/1989 |
| EP | 0 172 724 B1 | 7/1991 |
| EP | 0 272 149 B1 | 3/1992 |
| EP | 0 489 967 A1 | 6/1992 |
| EP | 0 497 607 B1 | 8/1992 |
| EP | 0 567 704 B1 | 11/1993 |
| EP | 1 033 141 A1 | 9/2000 |
| EP | 1 601 386 B1 | 12/2003 |
| JP | 63077948 | 4/1988 |
| JP | 02303818 | 12/1990 |
| JP | 03193047 | 8/1991 |
| JP | 2-684217 | 12/1997 |
| WO | WO89/02754 A1 | 4/1989 |
| WO | WO91/09633 A1 | 7/1991 |
| WO | WO96/11226 A2 | 4/1996 |
| WO | WO96/25469 A1 | 8/1996 |
| WO | WO97/00163 A1 | 1/1997 |
| WO | WO97/23577 A1 | 7/1997 |
| WO | WO99/57201 A1 | 11/1999 |
| WO | WO 00/09173 A1 | 2/2000 |
| WO | WO 00/74916 A1 | 12/2000 |
| WO | WO 01/24839 A1 | 4/2001 |
| WO | WO 01/43788 A2 | 6/2001 |
| WO | WO 02/43743 A1 | 6/2002 |
| WO | WO 02/066087 A1 | 8/2002 |
| WO | WO 03/022317 A1 | 3/2003 |
| WO | WO 03/047636 A2 | 6/2003 |
| WO | WO 03/053484 A1 | 7/2003 |
| WO | WO 04/080498 A1 | 9/2004 |
| WO | WO 2004/080499 A1 | 9/2004 |
| WO | WO 2005/056067 A1 | 6/2005 |
| WO | WO 2005/056069 A1 | 6/2005 |
| WO | WO 2005/056070 A1 | 6/2005 |

OTHER PUBLICATIONS

Park et al.; "Preparation and Characterization of Water-Swellable Natural Rubbers"; Journal of Applied Polymer Science; vol. 80, 2001; pp. 115-121.

Hageman, H.J.; "Photoinitiators for Free Radical Polymerization"; Progress in Organic Coatings, 13 (1985) pp. 123-150.

Wente et al; "Manufacture of Superfine Organic Fibers"; Report No. 4364 of the Naval Research Laboratory, published May 25, 1954.

Wente; "Superfine Thermoplastic Fibers"; Industrial and Engineering Chemistry; vol. 48, No. 8, pp. 1342-1346; Aug. 1956.

Wright et al.; "The Comparative Efficacy of Two Antimicrobial Barrier Dressings: In vitro Examination of Two Controlled Release of Silver Dressings"; Wounds 10(6); 179-188, 1998 © Health Management Publications, Inc.

ASTM D2857-93 "Standard Practice for Dilute Solution Viscosity of Polymers." Annual Book of ASTM Standards, vol. 08.01.

Nesbitt and Sandmann "Solubility Studies of Silver Sulfadiazine." 1977 *J. Pharm. Sci.* 66(4):519-522.

U.S. Appl. No. 11/550,440, filed on Oct. 18, 2002; and entitled "Antimicrobial Articles and Methods of Manufacture.".

U.S. Appl. No. 11/550,434, filed on Oct. 18, 2002; and entitled "Antimicrobial Atricles and Methods of Manufacture.".

* cited by examiner

ABSORBENT POLYMER COMPOSITIONS, MEDICAL ARTICLES, AND METHODS

BACKGROUND

Absorbent polymer compositions, particularly in the form of a foam, are useful in fluid management applications such as medical wound dressings and wound packing materials that absorb human sera. Conventional absorbent polymer foams typically include (1) closed cell foams prepared by introducing gas cells into the polymer by either thermal decomposition of chemical foaming agents or blending of gasses with polymer/hydrocolloid blends, or (2) open cell foams prepared by blending gasses with polymerizing hydrophilic polymers such as polyether-polyurethane pre-polymers. Absorbent foams prepared by method (2) have fast absorbency of human sera but do not retain the fluid upon little or no applied pressure. Absorbent foams prepared by method (1) pose difficult manufacturing issues with respect to maintaining the closed cell structure after extrusion forming due to inadequate cooling and subsequent coalescence and collapse of the closed cell structure that leads to a loss of void space.

Consequently, there is a need to provide foamed hydrocolloids that have sufficient initial uptake of aqueous fluids to facilitate fluid management of low to medium exuding wounds and a facile process for providing a composition having stabilized foam morphology.

SUMMARY OF THE INVENTION

In a first aspect, the present invention is directed to an absorbent polymer composition that includes a polymeric material, absorbent particles, and thermally expandable microspheres. In a second aspect, the present invention is an absorbent polymer foam composition that includes a polymeric material, absorbent particles, and thermally expanded microspheres. Herein, the absorbent particles and expandable microparticles are two distinct materials.

Preferably, the absorbent particles are provided in a matrix (e.g., a hydrocarbon oil) and form an emulsion (e.g., an inverse emulsion). Such emulsions are often referred to simply as "hydrocolloid."

In certain embodiments, the absorbent particles are superabsorbent. Herein, "absorbent" means that a material is capable of absorbing water or bodily fluids, and "superabsorbent" means that the material will absorb at least 100% of its weight.

Preferably, a polymer foam composition of the present invention that includes thermally expanded microspheres has a density less than 0.8 gram per cubic centimeter (cc), preferably less than 0.7 gram per cc.

In a particularly preferred embodiment, the present invention provides a polymer foam composition that includes: a polymeric material; a hydrocolloid comprising superabsorbent particles; and thermally expanded microspheres; wherein the polymer foam has a density of less than 0.8 gram per cubic centimeter.

In another embodiment, the present invention features an absorbent polymer foam composition that is preparable by a method that includes: combining a polymeric material, absorbent particles (preferably in the form of a hydrocolloid), and thermally expandable microspheres at a temperature below the expansion temperature of the microspheres to form a mixture; and increasing the temperature of the mixture above the expansion temperature of the thermally expandable microspheres.

In yet another embodiment, the present invention provides a method that includes: combining a polymeric material, absorbent particles (preferably in the form of a hydrocolloid), and thermally expandable microspheres to form a mixture in an extruder at a temperature below the expansion temperature of the microspheres; and increasing the temperature of the mixture above the expansion temperature of the thermally expandable microspheres during extrusion. Preferably, the resultant foamed composition has a density less than 0.8 gram per cubic centimeter (cc) (preferably less than 0.7 gram per cc) is formed.

The present invention also provides medical articles that include the polymer compositions. The medical articles can be any of a wide variety of products, but preferably are wound dressings and wound packing materials.

The present invention also provides methods of making and using the polymer compositions.

As used herein, "a," "an," "the," "at least one," and "one or more" are used interchangeably. Also herein, the recitations of numerical ranges by endpoints include all numbers subsumed within that range "e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments.

DETAILED DESCRIPTION OF ILLUSTRATIVE EMBODIMENTS OF THE INVENTION

The present invention provides polymer compositions that include a polymeric material, absorbent particles (which are preferably provided in the form of a hydrocolloid), an optional bioactive agent, and thermally expandable microspheres. The polymeric material can include a mixture of polymers. It can also include a pressure sensitive adhesive if desired. The polymer composition can be in a wide variety of forms, such as an extruded film (e.g., having a thickness of 0.5 millimeter (mm) to 10 mm), a coating, a hydrocolloid (i.e., a material that contains particles in a second phase, typically hydrophilic particles dispersed in a lipophilic phase (e.g., hydrophobic oil)), a molded article, etc.

The polymer compositions are preferably heated to expand the thermally expandable microspheres to provide a foam, such as an absorbent foam. Preferably, such a polymer foam composition with expanded microspheres therein has a density of less than 0.8 gram per cubic centimeter (cc), preferably less than 0.7 gram per cc.

Expansion of the thermally expandable microspheres can be carried out under pressure, such as that experienced in an extruder, or under ambient conditions such as that found in an air-circulating oven.

Preferably, the absorbent polymer foam composition is preparable by a method that includes combining components that include a polymeric material, absorbent particles (preferably in the form of a hydrocolloid), an optional bioactive agent, and thermally expandable microspheres at a temperature below the expansion temperature of the microspheres during extrusion such that a foamed composition having a density of less than 0.8 gram per cubic centimeter (cc) (preferably less than 0.7 gram per cc) is formed.

It has been discovered that absorbent foams of the present invention that have been formed by extruding the material and expanding the microspheres in the extruder have substantially higher initial uptake of aqueous fluids compared to: (1) un-foamed compositions (with or without unexpanded microspheres); (2) foams prepared via thermal decomposition of chemical foaming agents; and (3) foams prepared from extruded films containing thermally expandable microspheres that have been expanded after extrusion such as by thermal oven exposure.

Significantly, preferred compositions of the present invention demonstrate a surprising rate of absorbency. For example, deionized water absorbency (wet/dry weight) at 2 hours of swelling time is preferably at least 10%, and more preferably at least 20%, higher than the same polymer composition unfoamed or foamed using chemical foaming agents.

Polymeric Material

A variety of different polymers, as well as mixtures thereof, may be used for the polymeric material (i.e., polymeric matrix). Preferably, such polymers are those that are suitable for melt processing, particularly extrusion processing. As is well understood in the art, a wide range of physical properties of the polymer compositions can be obtained by selection of the types and amounts of different polymers.

Polymeric materials used to prepare the absorbent polymer compositions of the present invention are melt-processible when they are fluid or pumpable, and they do not significantly degrade or gel at the temperatures used to melt process (e.g., extruding or compounding) the composition (e.g., 50° C. to 300° C.). Preferably, such materials have a melt viscosity of 10 poise to 1,000,000 poise, as measured by capillary melt rheometry at the processing temperatures and shear rates employed in extrusion. Typically, suitable materials possess a melt viscosity within this range at a temperature of 125° C. to 175° C. and at a shear rate of approximately 100 seconds$^{-1}$ (s$^{-1}$).

If multiple polymer components are to be blended, preferably, each of the components has similar melt viscosity. The ability to form a finely dispersed morphology is related to a ratio of the shear viscosity of the components at melt mixing temperatures. Shear viscosity is determined using capillary rheometry at a shear rate approximating extrusion blending conditions, that is, 100 s$^{-1}$ and 175° C. When a higher viscosity component is present as the minor component, the viscosity ratio of minor to major components is preferably less than 20:1, more preferably less than 10:1. When a lower viscosity material is present as the minor component, the viscosity ratio of minor to major components are preferably greater than 1:20, more preferably greater than 1:10. The melt viscosities of individual components may be altered by the addition of plasticizers, tackifiers or solvents or by varying mixing temperatures.

The organic polymers suitable for the matrix of the polymer compositions of the present invention can be elastomeric, thermoplastic, or both.

Elastomeric polymers useful in the invention are typically materials that form one phase at 21° C., have a glass transition temperature less than 0° C., and exhibit elastomeric properties. The elastomeric polymers include, but are not limited to, polyisoprenes, styrene-diene block copolymers, natural rubber, polyurethanes, polyether-block-amides, poly-alpha-olefins, (C1–C20)acrylic esters of meth (acrylic) acid, ethylene-octene copolymers, and combinations thereof. Elastomeric materials useful in the present invention include, for example, natural rubbers such as CV-60 (a controlled viscosity grade natural rubber having Mooney viscosity of 60 +/− 5 ML, 1+4 at 100° C., available as an International commodity); butyl rubbers, such as Exxon Butyl 268 available from Exxon Chemical Co., Houston, Tex.; synthetic poly-isoprenes such as CARIFLEX IR309, available from Kraton Polymers, Houston, Tex., and NATSYN 2210, available from Goodyear Tire and Rubber Co., Akron, Ohio; ethylene-propylenes; polybutadienes; polyisobutylenes such as VISTANEX MM L-80, available from ExxonMobil Chemical Co.; and styrene-butadiene random copolymer rubbers such as AMERIPOL 1011A, available from BF Goodrich of Akron, Ohio.

Thermoplastic polymers useful in the invention include, for example, polyolefins such as isotactic polypropylene; low density or linear low density polyethylene; medium density polyethylene; high density polyethylene; polybutylene; polyolefin copolymers or terpolymers, such as ethylene/propylene copolymer and blends thereof-, ethylene-vinyl acetate copolymers such as ELVAX 260, available from E. I. DuPont de Nemours & Co., Wilmington, Del.; ethylene acrylic acid copolymers; ethylene methacrylic acid copolymers such as SURLYN 1702, available from E. I. DuPont de Nemours & Co.; polymnethylmethacrylate; polystyrene; ethylene vinyl alcohol; polyester; amorphous polyester; polyamides; fluorinated thermoplastics such a polyvinylidene fluoride; polytetrafluoroethylene; fluorinated ethylene/propylene copolymers; halogenated thermnoplastics such as a chlorinated polyethylene; and combinations thereof. Other exemplary thermoplastic polymers are disclosed in International Publication No. WO 97/23577.

Thermoplastic elastomeric polymers useful in the invention are typically materials that form at least two phases at 21° C., flow at a temperature greater than 50° C. and exhibit elastomeric properties. Thermoplastic elastomeric materials useful in the present invention include, for example, linear, radial, star and tapered styrene-isoprene block copolymers such as KRATON D1107P, available from Kraton Polymers, and EUROPRENE SOL TE 9110, available from EniChem Elastomers Americas, Inc. Houston, Tex., linear styrene-(ethylene/butylene) block copolymers such as KRATON G1657 available from Kraton Polymers, linear styrene-(ethylene/propylene) block copolymers such as KRATON G1657X available from Kraton Polymers, styrene-isoprene-styrene block copolymers such as KRATON D1119P available from Kraton Polymers, linear, radial, and star styrene-butadiene block copolymers such as KRATON D1118X, available from Kraton Polymers, and EUROPRENE SOL TE 6205 available from EniChem Elastomers Americas, Inc., polyetheresters such as HYTR-EL G3548, available from E. I. DuPont de Nemours & Co., and poly-alpha-olefin based thermoplastic elastomeric materials such as those represented by the formula —(CH$_2$—CHR) where R is an alkyl group containing 2 to 10 carbon atoms and poly-alpha-olefins based on metallocene catalysis such as ENGAGE EG8200, an ethylene/1-octene copolymer available from DuPont Dow Elastomers Co., Wilmington, Del. Other exemplary thermoplastic elastomers are disclosed in International Publication No. WO 96/25469.

For certain embodiments, preferably, the polymeric material includes a pressure-sensitive adhesive (PSA). It should be noted that the polymers do not need to possess pressure-sensitive properties to be useful in the invention. Different polymers may be used in combination and the particular polymer is selected based upon the desired properties of the final foam-containing article.

Pressure-sensitive adhesives useful in the present invention include, but are not limited to, natural rubbers, synthetic rubbers, styrene block copolymers, elastomers, polyurethanes, polyvinyl ethers, acrylics, poly-α-olefins, silicones, and blends thereof.

Useful natural rubber PSAs generally contain masticated natural rubber, from 25 parts to 300 parts of one or more tackifying resins to 100 parts of natural rubber, and typically from 0.5 to 2.0 parts of one or more antioxidants. Natural rubber may range in grade from a light pale crepe grade to a darker ribbed smoked sheet and includes such examples as CV-60, a controlled viscosity rubber grade, and SMR-5, a ribbed smoked sheet rubber grade. Tackifying resins used with natural rubbers generally include, but are not limited to, wood rosin and its hydrogenated derivatives; terpene resins of various softening points, and petroleum-based resins, such as, the ESCOREZ 1300 series of C5 aliphatic olefin-derived resins from Exxon Chemical Co., and PICCOLYTE S series, poly-terpenes from Hercules, Inc., Resins Division, Wilmington, Del. Antioxidants are used to retard the oxidative attack on natural rubber, which can result in loss of the cohesive strength of the natural rubber adhesive. Useful antioxidants include, but are not limited to, amines, such as N-N'di-beta-naphthyl-1,4-phenylenediamine, available as AGERITE D from R.T. Vanderbilt Co., Norwalk, Conn.; phenolics, such as 2,5-di-(t-amyl) hydroquinone, available as SANTOVAR A available from Monsanto Chemical Co., tetrakis[methylene 3-(3',5'-di-tert-butyl-4'-hydroxyphenyl) propianate]methane, available as IRGANOX 1010 from Ciba Specialty Chemicals Inc., Tarrytown, N.J., and 2-2'-methylenebis(4-methyl-6-tert butyl phenol), available as Antioxidant 2246 from Cytec Industries Inc., West Patterson, N.J.; and dithiocarbamates, such as zinc dithiodibutyl carbamate. Other materials can be added to natural rubber adhesives for example, plasticizers, pigments, and curing agents to partially vulcanize the pressure-sensitive adhesive.

Another useful class of PSAs comprises synthetic rubber. Such adhesives are generally rubbery elastomers, which are either self-tacky or non-tacky which are made tacky with tackifiers. Self-tacky synthetic rubber PSAs include, for example, butyl rubber, a copolymer of isobutylene with less than 3 percent isoprene, poly-isobutylene, a homo-polymer of isoprene, poly-butadiene, such as TAKTENE 220 available from Bayer Corp., Pittsburgh, Pa., and styrene/butadiene rubber. Butyl rubber PSAs often contain an antioxidant such as zinc dibutyl dithiocarbamate. Poly-isobutylene pressure-sensitive adhesives do not usually contain antioxidants. Synthetic rubber pressure-sensitive adhesives are also generally easier to melt process. They typically comprise poly-butadiene or styrene/butadiene rubber, from 10 parts to 200 parts of a tackifier, and generally from 0.5 to 2.0 parts per 100 parts rubber of an antioxidant such as IRGANOX 1010 from Ciba Specialty Chemicals. An example of a synthetic rubber is AMERIPOL 1011A, a styreneibutadiene rubber available from BF Goodrich. Tackifiers useful for synthetic rubber include derivatives of rosins such as FORAL 85 stabilized rosin ester from Hercules, Inc.; and synthetic hydrocarbon resins such as the PICCOLYTE A series poly-terpenes from Hercules, Inc., the ESCOREZ 1300 series and the ESCOREZ 2000 Series of C9 aromatic/aliphatic olefin-derived resins both from Exxon Chemical Co, and poly-aromatic C9 resins, such as the PICCO 5000 series of aromatic hydrocarbon resins, from Hercules, Inc. Other materials can be added for special purposes, including hydrogenated butyl rubber, pigments, plasticizers, liquid rubbers, such as VISTANEX LMMH poly-isobutylene liquid rubber available from ExxonMobil Chemical Co., and curing agents to partially vulcanize the adhesive.

Styrene block copolymer PSAs generally comprise elastomers of the A-B or A-B-A type, where A represents a thermoplastic polystyrene block and B represents a rubbery block of poly-isoprene, poly-butadiene, poly(ethylene/propylene), or poly(ethylene/butylene), and resins. Examples of block copolymers useful in block copolymer PSAs include linear, radial, star and tapered styrene-isoprene block copolymers such as KRATON D1107P, available from Kraton Polymers Co., and EUROPRENE SOL TE 9110, available from EniChem Elastomers Americas, Inc.; linear styrene-(ethylene/butylene) block copolymers such as KRATON G1657, available from Kraton Polymers Co.; linear styrene-(ethylene/propylene) block copolymers such as KRATON G1750X, available from Kraton Polymers Co.; and linear, radial, and star styrene-butadiene block copolymers such as KRATON D1118X, available from Kraton Polymers Co., and EUROPRENE SOL TE 6205, available from EniChem Elastomers Americas, Inc. The polystyrene blocks tend to form domains that cause the block copolymer PSAs to have two-phase structures. Resins that associate with the rubber phase generally develop tack in the pressure-sensitive adhesive. Examples of rubber phase associating resins include aliphatic olefin-derived resins, such as the ESCOREZ 1300 series available from Exxon Chemical Co., and the WINGTACK series, available from Goodyear Tire & Rubber Co.; rosin esters, such as the FORAL series and the STAYBELITE Ester 10, both available from Hercules, Inc.; hydrogenated hydrocarbons, such as the ESCOREZ 5000 series, available from Exxon Chemical Co.; poly-terpenes, such as the PICCOLYTE A series; and terpene phenolic resins derived from petroleum or terpentine sources, such as PICCOFYN A100, available from Hercules, Inc. Resins that associate with the thermoplastic phase tend to stiffen the pressure-sensitive adhesive. Thermoplastic phase associating resins include poly-aromatics, such as the PICCO 6000 series of aromatic hydrocarbon resins, available from Hercules, Inc.; coumarone-indene resins, such as the CUMAR series, available from Neville Chemical Company, Pittsburgh, Pa.; and other high-solubility parameter resins derived from coal tar or petroleum and having softening points above 85° C., such as the AMOCO 18 series of alphamethyl styrene resins, available from Amoco Chemicals, Warrensville Heights, Ohio, PICCO-VAR 130 alkyl aromatic poly-indene resin, available from Hercules, Inc., and the PICCOTEX series of alphamethyl styrene/vinyl toluene resins, available from Hercules, Inc. Other materials can be added to styrene block copolymers for special purposes, including rubber phase plasticizing hydrocarbon oils, such as Polybutene-8 from Chevron Phillips Chemical Co. LP, Houston, Tex., KAYDOL available from Witco Corp., Greenwich, Conn., and SHELLFLEX 371 available from Kraton Polymers Co.; pigments; antioxidants, such as IRGANOX 1010 and IRGANOX 1076, both available from Ciba Specialty Chemical Inc., BUTAZATE, available from Uniroyal Chemical Co., Middlebury, Conn., CYANOX LDTP, available from Cytec Industries, Inc., West Paterson, N.J., and BUTASAN, available from Monsanto Co.; anti-ozonants, such as NBC, a nickel dibutyldithiocarbamate, available from E. I. DuPont de Nemours & Co.; liquid rubbers such as VISTANEX LMMH poly-isobutylene rubber available from ExxonMobil Chemical Co., Houston, Tex.; and ultraviolet light inhibitors, such as IRGANOX 1010 and TINUVIN P, available from Ciba Specialty Chemical Inc.

Polyvinyl ether PSAs are generally blends of homo-polymers of vinyl methyl ether, vinyl ethyl ether or vinyl iso-butyl ether, or blends of homo-polymers of vinyl ethers and copolymers of vinyl ethers and acrylates to achieve desired pressure-sensitive properties. Depending on the degree of polymerization, homo-polymers may be viscous oils, tacky soft resins or rubber-like substances. Polyvinyl ethers used in polyvinyl ether adhesives include polymers based on: vinyl methyl ether such as LUTANOL M 40, available from BASF Corp., Mount Olive, N.J., and GANTREZ M 574 and GANTREZ 555, available from International Specialty Products, Inc. Wayne, N.J.; vinyl ethyl ether such as LUTANOL A 25, LUTANOL A 50 and LUTANOL A 100; vinyl isobutyl ether such as LUTANOL 130, LUTANOL 160, LUTANOL IC, LUTANOL 160D and LUTANOL 165D; methacrylate/vinyl isobutyl ether/acrylic acid such as ACRONAL 550 D, all available from BASF Corp. Antioxidants useful to stabilize the poly-vinylether pressure-sensitive adhesive include, for example, IRGANOX 1010 available from Ciba Specialty Chemical Inc., and Antioxidant ZKF all available from Bayer Corp. Other materials can be added for special purposes as described in BASF Corp. literature including tackifier, plasticizer, pigment, and combinations thereof.

Acrylic pressure-sensitive adhesive polymers can be formed by polymerizing one or more (meth)acrylic esters of non-tertiary alkyl alcohols, with the alkyl groups typically having form 1 to 20 carbon atoms (e.g., from 3 to 18 carbon atoms). Suitable acrylate monomers include methyl acrylate, ethyl acrylate, n-butyl acrylate, lauryl acrylate, 2-ethylhexyl acrylate, cyclohexyl acrylate, iso-octyl acrylate, octadecyl acrylate, nonyl acrylate, decyl acrylate, dodecyl acrylate, and combinations thereof. The corresponding methacrylates are useful as well. Also useful are aromatic acrylates and methacrylates, e.g., benzyl acrylate, cyclobenzyl acrylate, and combinations thereof.

Optionally, one or more mono-ethylenically unsaturated co-monomers may be polymerized with the (meth)acrylate monomers; the particular amount of co-monomer is selected based upon the desired properties of the polymer. One group of useful co-monomers includes those having a homo-polymer glass transition temperature greater than the glass transition temperature of the acrylate homo-polymer. Examples of suitable co-monomers in this group include acrylic acid, acrylamide, methacrylamide, substituted acrylamides such as N,N-dimethyl acrylamide, itaconic acid, methacrylic acid, acrylonitrile, methacrylonitrile, vinyl acetate, N-vinyl pyrrolidone, isobornyl acrylate, cyano ethyl acrylate, N-vinylcaprolactam, maleic anhydride, hydroxy-alkylacrylates, N,N-dimethyl aminoethyl (meth)acrylate, N,N-diethylacrylamide, beta-carboxyethyl acrylate, vinyl esters of neodecanoic, neononanoic, neopentanoic, 2-ethylhexanoic, or propionic acids (e.g., available from Union Carbide Corp. of Danbury, Conn. under the trade designation VYNATES), vinylidene chloride, styrene, vinyl toluene, alkyl vinyl ethers, and combinations thereof. A second group of monoethylenically unsaturated co-monomers which may be polymerized with the acrylate or methacrylate monomers includes those having a homo-polymer glass transition temperature less than the glass transition temperature of the acrylate homo-polymer. Examples of suitable co-monomers falling within this class include ethyloxy-ethoxy ethyl acrylate (Tg=−71° C.), a methoxypolyethylene glycol 400 acrylate (Tg=−65° C.; available from Shin Nakamura Chemical Co., Ltd., Tokyo, JP, under the designation "NK Ester AM-90G"), and combinations thereof.

Poly-α-olefin PSAs, also called a poly(1-alkene) pressure-sensitive adhesives, generally comprise either a substantially uncrosslinked polymer or a uncrosslinked polymer that may have radiation activatable functional groups grafted thereon as described in U.S. Pat. No. 5,209,971 (Babu et. al.). The poly-alpha-olefin polymer may be self-tacky and/or include one or more tackifying materials. If uncrosslinked, the inherent viscosity of the polymer is generally between 0.7 and 5.0 deciliters per gram as measured by ASTM D 2857-93, "Standard Practice for Dilute Solution Viscosity of Polymers". In addition, the polymer generally is predominantly amorphous. Useful poly-alpha-olefin polymers include, for example, three to eighteen carbon (C3–C18) poly(1-alkene) polymers, preferably C5–C12 alpha-olefins and copolymers of those with C3 and more preferably C6–C8 and copolymers of those with C3. Tackifying materials are typically resins that are miscible in the poly-alpha-olefin polymer. The total amount of tackifying resin in the poly-alpha-olefin polymer ranges from 0 to 150 parts by weight per 100 parts of the poly-alpha-olefin polymer depending on the specific application. Useful tackifying reins include resins derived by polymerization of C5 to C9 unsaturated hydrocarbon monomers, polyterpenes, synthetic polyterpenes and the like and combinations thereof. Examples of such commercially available resins based on a C5 olefin fraction of this type are WINGTACK 95 and WINGTACK 15 tackifying resins from Goodyear Tire & Rubber Co. Other hydrocarbon resins include REGALREZ 1078 and REGALREZ 1126 available from Hercules, Inc., and ARKON P115 available from Arakawa Chemical USA, Inc., Chicago, Ill. Other materials can be added, including antioxidants, fillers, pigments, radiation activated crosslinking agents, and combinations thereof.

Silicone PSAs comprise two major components, a polymer or gum, and a tackifying resin. The polymer is typically a high molecular weight polydimethylsiloxane or polydimethyldiphenylsiloxane, that contains residual silanol functionality (SiOH) on the ends of the polymer chain, or a block copolymer comprising polydiorganosiloxane soft segments and urea terminated hard segments. The tackifying resin is generally a three-dimensional silicate structure that is end-capped with trimethylsiloxy groups ($OSiMe_3$) and also contains some residual silanol functionality. Examples of tackifying resins useful with silicones include SR 545, from General Electric Co., Silicone Resins Division, Waterford, N.Y., and MQD-32-2 from Shin-Etsu Silicones of America, Inc., Torrance, Calif. Manufacture of typical silicone pressure-sensitive adhesives is described in U.S. Pat. No. 2,736,721 (Dexter). Manufacture of silicone urea block copolymer pressure-sensitive adhesive is described in U.S. Pat. No. 5,214,119 (Leir et al). Other materials that can be added to silicones, include pigments, plasticizers, and fillers. Fillers are typically used in amounts from 0 parts to 10 parts per 100 parts of silicone pressure-sensitive adhesive. Examples of fillers that can be used with silicones include zinc oxide, silica, carbon black, pigments, metal powders, calcium carbonate and combinations thereof.

Solid elastomeric gels produced by the process described in International Publication No. 97/00163 are also useful polymers in the present invention. Generally, the method described in WO 97/00163 is for making solid elastomeric gel from styrene block copolymer (e.g., styrene-isoprene-styrene, styrene-ethylenebutylene-styrene) and plasticizers. The method includes the steps of: (1) providing an extruder having multiple in-feed sections with each followed by a mixing section along a barrel of the extruder; (2) introducing the copolymer into one of the in-feed sections of the operating extruder; (3) heating and shearing the copolymer in a subsequent mixing section; (4) introducing the plasticizer to the copolymer through at least one of the feeding sections in a pattern and at a rate that produces solid elastomeric gel at room temperature that will retain its shape after repeated compression and decompression of the gel; and (5) ejecting the gel from the extruder. The ejecting step may include ejecting the gel through a die to form a length of the gel having a predetermined cross-section, and the method may further include (6) cutting the extruded gel into lengths to form pieces of the gel with uniform cross sections that can be used in pads. Alternatively, the method can further include the step of (6) injecting the ejected gel into a mold having a pre-determined shape.

Various combinations of the foregoing polymers can be used for desired effects.

The polymer may be crosslinked by adding a crosslinking compound or through electron beam or gamma radiation. A crosslinking compound can be a multi-ethylenically unsaturated compound wherein the ethylenic groups are vinyl groups, allyl groups, and/or methallyl groups bonded to nitrogen, oxygen, or carbon atoms. Exemplary compounds for crosslinking vinyl-containing polymers include, but are not limited to, divinyl, diallyl or dimethallyl esters (e.g., divinyl succinate, divinyl adipate, divinyl maleate, divinyl oxalate, divinyl malonate, divinyl glutarate, diallyl itaconate, diallyl maleate, diallyl fumarate, diallyl diglycolate, diallyl oxalate, diallyl adipate, diallyl succinate, diallyl azelate, diallyl malonate, diallyl glutarate, dimethallyl maleate, dimethallyl oxalate, dimethallyl malonate, dimethallyl succinate, dimethallyl glutarate, and dimethallyl adipate), divinyl, diallyl or dimethallyl ethers (e.g., diethyleneglycol divinyl ether, butanediol divinyl ether, ethylene glycol divinyl ether, ethylene glycol diallyl ether, diethylene glycol diallyl ether, butane diol diallyl ether, ethylene glycol dimethallyl ether, diethylene glycol dimethallyl ether, and butane diol dimethallyl ether), divinyl, diallyl or dimethallyl amides including bis(N-vinyl lactams), (e.g., 3,3'-ethylidene bis(N-vinyl-2-pyrrolidone)), and divinyl, diallyl or dimethallyl ureas. Various combinations of such crosslinking agents can be used if desired.

Absorbant Particles

The addition of absorbent particles, preferably in the form of a hydrocolloid, to the polymer imparts hydrophilic character to the composition. The particles used in the present invention may be any synthetically prepared or naturally occurring polymer capable of absorbing aqueous fluids including human sera. Varieties of particles within the scope of the present invention include synthetic polymers prepared from single or multiple monomers, naturally occurring hydrophilic polymers or chemically modified naturally occurring hydrophilic polymers.

Non-limiting examples of such particles include polyhydroxyalkyl acrylates and methacrylates, polyvinyl lactams, polyvinyl alcohols, polyoxyalkylenes, polyacrylamides, polyacrylic acid, polystyrene sulfonates, natural or synthetically modified polysaccharides, alginates, xanthan gums, guar gums, cellulosics, and combinations thereof.

When used in medical applications, the particles are preferably dermatologically acceptable and non-reactive with the skin of the patient or other components of the foamed absorbent composition including any antimicrobial agents that may be present in the composition.

Desirably, the particles include a synthetic polymer that may be either linear or crosslinked. Non-limiting examples of synthetic hydrocolloids include polymers prepared from N-vinyl lactams, e.g. N-vinyl-2-pyrrolidone, 5-methyl-N-vinyl-2-pyrrolidone, 5-ethyl-N-vinyl-2-pyrrolidone, 3,3-dimethyl-N-vinyl-2-pyrrolidone, 3-methyl-N-vinyl-2-pyrrolidone, 3-ethyl-N-vinyl-2-pyrrolidone, 4-methyl-N-vinyl-2-pyrrolidone, 4-ethyl-N-vinyl-2-pyrrolidone, N-vinyl-2-valerolactam, N-vinyl-2-caprolactam, and combinations thereof.

Other monomers useful to prepare absorbent particles include hydroxyalkyl acrylates and methacrylates (such as 2-hydroxyethyl acrylate, 2-hydroxyethyl methacrylate, 2-hydroxypropyl acrylate, 2-hydroxypropyl methacrylate, 2,3-dihydroxypropyl methacrylate), acrylic acid, methacrylic acid and a tertiary amino-methacrylimide (e.g., trimethylamino-methacrylimide), crotonic acid, pyridine, and combinations thereof.

Other monomers useful to prepare absorbent particles include water soluble amides (such as N-(hydroxymethyl)acrylamide and -methacrylamide, N-(3-hydroxpropyl)acrylamide, N-(2-hydroxyethyl) methacrylamide, N-(1,1-dimethyl-3-oxabutyl)acrylamide N-[2-(dimethylamine)ethyl] acrylamide and -methacrylamide, N-[3-(dimethylamino)-2-hydroxylpropyl]methacrylamide, and N-[1,1-dimethyl-2-(hydroxymethyl)-3-oxabutyl]acrylamide); water-soluble hydrazine derivatives (such as trialkylamine methacrylimide, and dimethyl-(2-hydroxypropyl)amine methacrylimide); mono-olefinic sulfonic acids and their salts (such as sodium ethylene sulfonate, sodium styrene sulfonate and 2-acrylamideo-2-methylpropanesulfonic acid); and the following monomers containing nitrogen in the non-cyclic or cyclic backbone of the monomer: 1-vinyl-imidazole, 1-vinyl-indole, 2-vinyl imidazole, 4-vinyl-imidazole, 2-vinyl-1-methyl-imidazole, 5-vinyl-pyrazoline, 3-methyl-5-isopropenyl-pyrazole, 5-methylene-hydantoin, 3-vinyl-2-oxazolidone, 3-methacrylyl-2-oxazolidone, 3-methacrylyl-5-methyl-2-oxazolidone, 3-vinyl-5-methyl-2-oxazolidone, 2- and 4-vinyl-pyridine, 5-vinyl-2-methyl-pyridine, 2-vinyl-pyridine-1-oxide, 3-isopropenyl-pyridine, 2- and 4-vinyl-piperidine, 2- and 4-vinyl-quinoline, 2,4-dimethyl-6-vinyl-s-triazine, 4-acrylyl-morpholine, and combinations thereof.

Other absorbent particles include polymers that are either naturally occurring or synthetically prepared. These materials include polyvinyl alcohol, polyoxyalkylenes, and such naturally occurring or synthetically modified materials as polysaccharides, gums, modified cellulosics, and combinations thereof.

Representative polysaccharides include starch, glycogen, hemicelluloses, pentosans, gelatin, celluloses, pectin, chitosan, and chitin. Representative gums include Arabic, Locust Bean, Guar, Agar, Carrageenan, Xanthan, Karaya, alginates, tragacanth, Ghatti, and Furcelleran gums. Representative modified celluloses include methyl cellulose, hydroxypropyl methyl cellulose, carboxymethylcellulose, and hydroxypropyl cellulose.

Useful absorbent particles of the present invention are preferably prepared by reverse-phase polymerization methods described in European Patent Specifications 0 172 724 B1 and 0 126 528 A2, which form inverse-emulsions having 0.2 to 10 micron diameter crosslinked hydrophilic polymer microparticles dispersed in hydrophobic oils (preferably the polymer is chosen to be miscible with the hydrophobic oil). These emulsions are commercially available under the trade designation of SALCARE from Ciba Specialty Chemicals. The hydrophilic polymers can be either anionic (e.g., 50 weight percentage solids sodium polyacrylate in mineral oil, available as SALCARE SC91) or cationic (e.g., 50 weight percentage solids methylene chloride quaternary ammonium salt of dimethylaminoethylmethacrylate in mineral oil, available as SALCARE SC95). Other absorbent particles can be prepared using a volatile solvent as described in European Patent Application 0 489 967 A1.

Crosslinking of the linear polymer chains of the absorbent particles may be desired to improve cohesive properties upon absorption of aqueous fluids. When such crosslinking is desired for polymers made from vinyl monomers discussed above, a multi-ethylenically unsaturated compound with the ethylenic groups being vinyl, allyl, or methallyl groups bonded to nitrogen, oxygen or carbon atoms can be used.

Non-limiting examples of crosslinking agents for vinyl containing polymers include divinyl, diallyl, or dimethallyl esters (e.g. ethylene glycol dimethacrylate, divinyl succinate, divinyl adipate, divinyl maleate, divinyl oxalate, divinyl malonate, divinyl glutarate, diallyl itaconate, diallyl maleate, diallyl fumarate, diallyl diglycolate, diallyl oxalate, diallyl adipate, diallyl succinate, diallyl azelate, diallyl malonate, diallyl glutarate, dimethallyl maleate, dimethallyl oxalate, dimethallyl malonate, dimethallyl succinate, dimethallyl glutarate, and dimethallyl adipate); divinyl, diallyl or dimethallyl ethers (e.g. diethyleneglycol divinyl ether, butane diol divinyl ether, ethylene glycol divinyl ether, ethylene glycol diallyl ether, diethylene glycol diallyl ether, butane diol diallyl ether, ethylene glycol dimethallyl ether, diethylene glycol dimethallyl ether, and butane diol dimethallyl ether); divinyl, diallyl or dimethallyl amides including bis(N-vinyl lactams), (e.g., 3,3'-ethylene bis(N-vinyl-2-pyrrolidone) and methylene-bis-acrylamide); and divinyl, diallyl and dimethallyl ureas. Various combinations of crosslinking agents can be used.

For n-vinyl lactams, the preferred crosslinking agents are diallyl maleate and 3,3'-ethylidene bis (N-vinyl-2-pyrrolidone). For acrylates and methacrylates, the preferred crosslinking agents are ethylene glycol dimethacrylate and methylene-bis-acrylamide. For polyvinyl lactams (e.g., poly-N-vinylpyrrolidone), the preferred crosslinking agents are diallyl maleate or 3,3'-ethylidene bis (N-vinyl-2-pyrrolidone).

Expandable Microspheres

The expandable microspheres useful in the invention feature a flexible, thermoplastic, polymeric shell and a core that includes a liquid and/or gas that expands upon heating above the expansion temperature of the microsphere. This expansion typically involves softening of the polymeric shell and expansion of the liquid or gas core. Preferably, the core material is an organic substance that has a lower boiling point than the softening temperature of the polymeric shell. Examples of suitable core materials include propane, butane, pentane, iso-butane, neo-pentane, and combinations thereof.

The choice of thermoplastic resin for the polymeric shell influences the mechanical properties of the foam. Accordingly, the properties of the foam may be adjusted through appropriate choice of microsphere, or by using mixtures of different types of microspheres. For example, acrylonitrile-containing resins are useful where high tensile and cohesive strength are desired, particularly where the acrylonitrile content is at least 50% by weight of the resin, more preferably at least 60% by weight, and even more preferably at least 70% by weight. In general, both tensile and cohesive strength increase with increasing acrylonitrile content. In some cases, it is possible to prepare foams having higher tensile and cohesive strength than the polymer matrix alone, even though the foam has a lower density than the matrix. This provides the capability of preparing high strength, low density foams.

Examples of suitable thermoplastic resins that may be used as the polymeric shell include (meth)acrylic acid esters such as poly-acrylate; acrylate-acrylonitrile copolymer; and methacrylate-acrylic acid copolymer. Vinylidene chloride-containing polymers such as vinylidene chloride-methacrylate copolymer, vinylidene chloride-acrylonitrile copolymer, acrylonitrile-vinylidene chloride-methacrylonitrile-methyl acrylate copolymer, and acrylonitrile-vinylidene chloride-methacrylonitrile-methyl methacrylate copolymer may also be used, but are not preferred where high strength is desired. In general, where high strength is desired, the microsphere shell preferably has no more than 20% by weight vinylidene chloride, more preferably no more than 15% by weight vinylidene chloride. Even more preferred for high strength applications microspheres have essentially no vinylidene chloride units.

Examples of suitable commercially available expandable polymeric microspheres include those available from Pierce Stevens, Buffalo, N.Y., under the trade designations MICROPEARL F30D, F80SD, and F100D. Also suitable are expandable polymeric microspheres available from Expancel, Inc., Duluth, Ga., under the designations EXPANCEL 551, EXPANCEL 461, and EXPANCEL 091. Each of these microspheres features an acrylonitrile-containing shell. In addition, the MICROPEARL F80SD and F100D, and EXPANCEL 091 microspheres have essentially no vinylidene chloride units in the shell.

Various combinations of expandable microspheres can be used. The amount of expandable microspheres is selected based upon the desired properties of the foam product. In general, the higher the microsphere concentration, the lower the density of the foam. In general, the amount of microspheres is preferably at least 0.1 part by weight, and more preferably at least 0.5 part by weight, based on 100 parts of polymer. The amount of microspheres is preferably at most 50 parts by weight, and more preferably at most 20 parts by weight, based on 100 parts of polymer.

Bioactive Agent

The polymer compositions of the present invention can include a bioactive agent. Examples include, but are not limited to, antimicrobial agents such as silver chloride, silver oxide, silver nitrate, silver acetate, silver lactate, silver sulfate, copper chloride, copper nitrate, copper acetate, copper lactate, copper sulfate, zinc chloride, zinc nitrate, zinc acetate, zinc lactate, and zinc sulfate. Other antimicrobial agents that can be used include parachlorometaxylenol, chlorhexidine and salts thereof, iodine, and iodophores, and antibiotics such as neomycin, bacitracin, and polymyxin B. Preferred compositions have more than one bioactive agent.

The bioactive agent can be present in the polymer composition in an amount to produce a desired effect (e.g., antimicrobial effect). Preferably, the bioactive agent is present in an amount such that the polymer composition is stable. In this context, "stable" means the composition does not turn black over a typical exposure time in the presence of at least one of the following types of radiation: visible light, ultraviolet light, electron beam, and gamma ray sterilization.

Optional Additives

The polymer compositions of the present invention can include a wide variety of optional additives (in addition to the additives discussed above in reference to PSAs). Examples include secondary bioactive agents, secondary absorbent particles, chemical foaming agents, physical foaming agents, swelling agents, fillers, pigments, dyes, plasticizers, tackifiers, crosslinking agents, ultraviolet and thermal stabilizers, antioxidants, colorants, extruding aids, chain transfer agents, and combinations thereof.

In certain embodiments, polymer compositions of the present invention can include fillers, which can be inorganic or organic. Examples of inorganic fillers include barytes, chalk, gypsum, kieserite, sodium carbonate, titanium dioxide, cerium oxide, silica dioxide, kaolin, carbon black, and hollow glass micro-beads. Examples of organic fillers include powders based on polystyrene, polyvinyl chloride, urea-formaldehyde and polyethylene. The fillers may be in the form of fibers, such as chopped fibers. Examples of suitable chopped fibers include glass fibers (typically 0.1 millimeter (mm) to 1 mm long) or fibers of organic origin such as, for example, polyester or polyamide fibers.

In order to confer color to the polymer compositions it is possible to use dyes or colored pigments of an organic or inorganic basis such as, for example, iron oxide or chromium oxide pigments or phthalocyanine- or monoazo-based pigments.

Method of Preparation

The following exemplary extrusion process can be used for preparing absorbent polymer foam compositions featuring a polymer matrix, absorbent particles (typically provided in the form of a hydrocolloid), an optional bioactive agent, and expandable polymer microspheres. In the process, polymer(s) is initially fed into a first extruder (typically a single-screw extruder) that softens and grinds the resin into small particles suitable for extrusion. The polymer will eventually form the polymer matrix of the foam. The polymer may be added to the first extruder in any convenient form, including pellets, billets, packages, strands, and ropes.

Next, the polymer, absorbent particles, and all other additives except the expandable microspheres are fed to a second extruder (e.g., a single or twin-screw extruder) at a point immediately prior to the kneading section of the extruder. Once combined, the polymer and additives are fed to the kneading zone of the second extruder where they are mixed well. The mixing conditions (e.g., screw speed, screw length, and temperature) are selected to achieve optimum mixing. Preferably, mixing is carried out at a temperature insufficient to cause microsphere expansion. It is also possible to use temperatures in excess of the microsphere expansion temperature, in which case, the temperature is decreased following mixing and prior to adding the microspheres.

Once the polymer, absorbent particles, and other additives (except the expandable microspheres) have been adequately mixed, expandable polymeric microspheres are added to the resulting mixture, at a downstream entrance to the second extruder, and melt-mixed to form an expandable extrudable composition. The purpose of the melt-mixing step is to prepare an expandable extrudable composition in which the expandable polymeric microspheres and other additives are distributed substantially homogeneously throughout the molten polymer. Typically, the melt-mixing operation uses one kneading block to obtain adequate mixing, although simple conveying elements may be used as well. The temperature, pressure, shear rate, and mixing time employed during melt-mixing are selected to prepare this expandable extrudable composition without causing the microspheres to expand or break; once broken, the microspheres are unable to expand to create a foam. Specific temperatures, pressures, shear rates, and mixing times are selected based upon the particular composition being processed.

Following melt-mixing, the absorbent expandable polymer composition is metered into an extrusion die (for example, a contact or drop die) through a length of transfer tubing using a gear pump that acts as a valve to control die pressure and thereby prevent premature expansion of the microspheres. The temperature within the die is preferably maintained at substantially the same temperature as the temperature within transfer tubing, and selected such that it is at or above the temperature required to cause expansion of the expandable microspheres. However, even though the temperature within transfer tubing is sufficiently high to cause microsphere expansion, the relatively high pressure within the transfer tubing prevents them from expanding. Once the composition enters the extrusion die, however, the pressure drops because the volume of the die is greater than the volume of the tubing. The pressure drop, coupled with heat transfer from the die, causes the microspheres to expand within the die, leading to foaming. The pressure within the die continues to drop further as the composition approaches the exit, further contributing to microsphere expansion within the die. The flow rate of polymer through the extruder and the die exit opening are maintained such that as the polymer composition is processed through the die, the pressure in the die cavity remains sufficiently low to allow expansion of the expandable microspheres before the polymer composition reaches the exit opening of the die.

The shape of the absorbent polymer foam is a result of the shape of the exit of the extrusion die. Although a variety of shapes may be produced, the foam is typically produced in the form of a continuous or discontinuous sheet.

Another continuous forming method involves directly contacting the extruded absorbent polymer foam to a rapidly moving plastic web or other suitable substrate. In this method, the extruded absorbent polymer foam can be applied to the moving web using a die having flexible die lips such as a reverse orifice coating die and other contact dies using rotating rods.

After extrusion, the absorbent polymer foam is preferably solidified by quenching using either a direct method, such as chill rolls or water baths, or an indirect method, such as air or gas impingement. This step arrests the continued expansion of the microspheres as they exit the die.

The foam may optionally be combined with a liner dispensed from a feed roll. Suitable materials for liners include silicone release liners, polyester films (e.g., polyethylene terephthalate films), and polyolefin films (e.g., polyethylene films). The liner and the foam are then laminated together between a pair of nip rollers. Following lamination, the foam is optionally exposed to radiation from an electron beam source to crosslink the foam; other sources of radiation (e.g., ion beam, gamma, and ultraviolet radiation) may be used as well. Crosslinking improves the cohesive strength of the foam. Following exposure, the laminate can be rolled up onto a take-up roll. Optionally, the rolled up laminate can be exposed to gamma radiation to crosslink the foam.

If desired, the smoothness of one or both of the foam surfaces can be increased by using a nip roll to press the foam against a chill roll after the foam exits die. It is also possible to emboss a pattern on one or both surfaces of the foam by contacting the foam with a patterned roll after it exits the die.

The foam may also be combined with one or more additional polymer compositions, e.g., in the form of layers, stripes, rods, etc., preferably by co-extruding additional extrudable polymer compositions with the microsphere-containing extrudable compositions. It is also possible to use a co-extrusion process such that a two-layer article is produced, or such that articles having more than three layers (e.g., 10–100 layers or more) are produced. This is accomplished by equipping the extrusion die with an appropriate feed block, or by using a multi-vaned or multi-manifold die as in U.S. Pat. No. 6,379,791 (Cernohous et al.). Multi-layer foam articles can also be prepared by laminating additional layers to the foam core, or to any of the co-extruded layers after the absorbent polymer foam exits the extrusion die.

Medical Articles

The polymer compositions of the present invention can be used in a wide variety of products, although they are preferably used in medical articles. Such medical articles can be in the form of a wound dressing, wound packing material, or other materials that are applied directly to or contact a wound.

Such articles may or may not include a backing. If a backing is desired, it may or may not be porous. Suitable materials are preferably flexible, and may be fabric, non-woven or woven polymeric films, metallic foils, paper, and/or combinations thereof. More specifically, film backings are useful with the polymer compositions of the present invention and include, for example, ethylene-propylene-diene rubbers, polyesters, poly-isobutylenes, polyolefins, polyolefin-based non-wovens, polyurethanes, vinyls including polyvinylchloride and ethylene-vinyl acetate, and/or combinations thereof. For particular purposes, the backing may be coated on one or both major surfaces, with a primer or a release agent, which may be a low-adhesion backsize (LAB) material. For example, when using a plasticized polyvinylchioride (PVC) backing, an embodiment of the present invention comprising a butadiene- or isoprene-containing polymer along with a polyisoprene-polyvinylpyridine (PI-PVP) compatibilizer has a particular advantage in that the composite PSA has an affinity for acidic PVC.

The backing can also be provided with stretch-release properties. Stretch-release refers to the property of an adhesive article characterized in that, when the article is pulled from a surface, the article detaches from the surface without leaving significant visible residue. For example, a film backing can be formed from a highly extensible and highly elastic composition comprising elastomeric and thermoplastic A-B-A block copolymers, having a low rubber modulus, a lengthwise elongation to break of at least 200%, and a 50% rubber modulus of not above 2,000 pounds/square inch (13.8 megapascals (MPa)). Such backings are described in U.S. Pat. No. 4,024,312 (Korpman). Alternatively, the backing can be highly extensible and substantially non-recoverable such as those described in U.S. Pat. No. 5,516,581 (Kreckel et al).

EXAMPLES

Objects and advantages of this invention are further illustrated by the following examples, but the particular materials and amounts thereof recited in these examples, as well as other conditions and details, should not be construed to unduly limit this invention.

Materials

KRATON D1107P—styrene-isoprene-styrene thermoplastic (SIS) elastomer available from Kraton Polymers, Houston, Tex.

KRATON G4609—52 wt-% KRATON G1651 and 48 wt-% KAYDOL mineral oil, available from Kraton Polymers.

KAYDOL OIL—naphthenic plasticizing oil available from Crompton/Witco Corp.

ESCOREZ 1310LC—aliphatic C5 tackifying resin compatible with isoprene block of KRATON D1107 available from Exxon Chemical Company.

IRGANOX 1010—antioxidant available from Ciba Specialty Chemicals, Tarrytown, N.Y.

SALCARE SC91—50 wt-% solids cosmetic grade emulsion having micro-particles of chemically crosslinked hydrophilic anionic sodium acrylates copolymer in mineral and paraffin oils available from Ciba Specialty Chemicals, High Point, N.C.

SALCARE SC95—50 wt-% solids cosmetic grade emulsion having micro-particles of chemically crosslinked hydrophilic cationic quaternary ammonium acrylate polymer [methylene chloride quaternary ammonium salt of 2-(dimethylamino)ethyl methacrylate] in mineral and paraffin oils available from Ciba Specialty Chemicals, High Point, N.C.

Silver Nitrate ($AgNO_3$)—99+% reagent grade; Formula Weight (FW) is 169.88; used as-received from Aldrich, Milwaukee, Wis.

CELOGEN OT—nitrogen based chemical foaming agent available from Uniroyal Chemical Co. that decomposes at 158–160° C.

MICROPEARL F100D—thermally expandable polymeric microsphere physical foaming agent available from Pierce and Stevens.

Deionized Water Absorbency Test

Samples were tested for their time-dependent absorbency of deionized (DI) water by placing the sample directly in the DI water at ambient temperature (approximately 22° C.). The sample was removed at a specified period of dwell time and patted lightly with a paper towel to remove surface moisture. The weight of the sample was then recorded and the sample was placed back into the DI water solution. The absorbency of the sample was calculated as the ratio of the weight of DI water absorbed per dry weight of the sample, or [(DI water-swollen weight–dry weight)/dry weight].

2 Hours % Live Bacteria Test

The effectiveness of a sample was tested using a L-7012, Bacterial Viability Kit, available from Molecular Probes, Eugene, Oreg. The procedure is outlined below using the red, propidium iodide dye, and green, SYTO 9 dye, contained in the kit to stain the live and dead bacteria.

Preparation of bacteria solution: *Staphylococcus aureus* bacteria were grown in Trypticase (Tryptic) Soy Broth (TSB) medium overnight. Bacteria were concentrated by centrifugation at 10,000× gravity for 15 minutes (min). Supernatant was removed and the pellet was re-suspended in MilliQ water (filtered through a 0.2 micrometer (micron or μm) pore-size filter) or in Butterfield phosphate buffer (from Hardy Diagnostics, Santa Maria, Calif.). Bacteria solution was diluted to the desired bacteria concentration ($10^7$ cells/milliliters) by measuring the optical density (OD) at 670 nm. For a control experiment, the bacteria solution was incubated with 70% isopropyl alcohol at room temperature for 1 hour (hr) to measure the killed bacteria control. Different volume of live and dead bacteria solutions were mixed to generate a range of percent live solution for calibration purposes.

Sample preparation: All prototypes were prepared by punching out a 1-inch (2.54-cm) diameter samples using a stainless steel punch; sometimes as indicated in the examples a 1-inch (2.54 cm) disk was further cut with scissors in eighths and then evaluated. The amount of sample was weighed, and then transferred to 50 milliliters (mL) sterile conical tubes.

Bacteria labeling and Anti-microbial testing: 7 mL of bacteria solution at initial concentration of approximately $1 \times 10^8$ bacteria/mL were pipetted into a 50 mL conical tube containing the sample. At the specified time (e.g., 2 hr), 50 micro-liter (μL) of the supernatant was pipetted into fluorescent measurement tube which already contained 450 μL of MiliQ water and premixed green dye and red dye solution (1.5 μL dye mixture for 500 μL bacteria solution) was added and the mixture was incubated for 15 minutes in the dark at room temperature. These solutions were then measured by flow cytometry. Cell viability was measured using the BD FACSCaliber flow cytometer (made by Becton Dickinson & Company, Franklin Lakes, N.J.). The flow cytometer is equipped with an argon-ion laser at 488 nanometers (nm) and 15 milliwatts (mW) output. Data acquisition and analysis were controlled using CellQuest software and PBPAC hardware interface. The light path contained a 488/10 nm blocking filter, then a 530/30 nm filter before the green PMT and a 585/42 nm long pass filter before the red PMT. The sampling rate was around 3000–7000 particles/second. The sheath fluid was FACSFlow by Becton Dickinson & Company. The instrument voltage was 5.5 Volt.

The live cell and dead bacteria responses were established with the 100 % live cell and 100% dead cell (for killed bacteria, bacteria solution was incubated with 70% isopropyl alcohol at room temperature for 1 hr) samples. Different volumes of live and dead bacteria solutions were mixed to generate a range of percent live solutions for calibration purposes. The sample results for bacteria killing ability were interpolated from the standard curve generated from calibration samples. Total bacteria concentration was determined by the measuring of the OD at 670 nm of the bacteria solution.

Examples 1–2 and Comparative Examples C1–C4

Examples 1–2 and Comparative Examples C1–C4 were prepared using a Werner Pfleiderer ZSK30 fully intermeshing and co-rotating twin-screw extruder (TSE) having a length to diameter ratio of 27 to 1 and nine barrel sections. KRATON D1107P pellets were gravimetrically fed into the feed throat (barrel 1) of the TSE using a KTRON gravimetric feeder. ESCOREZ 1310LC was melted at 340° F. (171° C.) and pumped into barrel 5. SALCARE SC91 inverse emulsion polymer was fed at room temperature (22° C.) into barrel 8 using a ZENITH gear pump. A foaming agent (either CELOGEN OT or MICROPEARL F100D) was gravimetrically fed into an auxiliary single-screw extruder conveying device attached to barrel 7. The temperature of the TSE was maintained at 300° F.(149° C.), 350° F.(177° C.), 400° F.(204° C.) and 250° F. (121° C.) for barrels 1, 2, 3 and 4–9, respectively. The measured polymer melt temperature at the discharging ZENITH gear pump at the end of the TSE was 297° F. (147° C.). The discharging ZENITH pump was maintained at 250° F. (121° C.) and the conveying hose and extrusion die temperatures were maintained at 275° F. (135° C.) for Comparative Examples C1–C4 and 325° F. (163° C.) for Examples 1–2. The TSE screw speed was 300 revolutions per minute (rpm) and the total extrusion throughput was approximately 17 pounds per hour (129 grams per minute). The mixtures were extruded through a 6 inches (15.2 centimeters) wide single orifice film die and into a nip formed by two polished and chromed steel rolls maintained at 40° F. (4.4° C.) and 0.040 inch (1.0 millimeter) gap. Two 0.002 inch (0.05 millimeter) thick release-coated polyethylene terephthalate (PET) films were contacted to each side of the extruded film to facilitate release of the extrudate from the chilled rolls. The nip speed was adjusted to maintain a constant speed of 3 feet per minute (0.9 meters per minute). Table 1 contains the compositional information for Examples 1–2 and Comparative Examples C1–C4.

TABLE 1

| Example No. | KRATON D1107P (wt-%) | ESCOREZ 1310LC (wt-%) | SALCARE SC91 (wt-%) | CELLOGEN OT (wt-%) | MICROPEARL F100D (wt-%) |
|---|---|---|---|---|---|
| C1 | 35.0 | 35.0 | 30.0 | 0 | 0 |
| C2 | 34.5 | 34.5 | 29.5 | 1.5 | 0 |
| C3 | 34.0 | 34.0 | 29.1 | 2.9 | 0 |
| C4 | 33.0 | 33.0 | 28.4 | 5.6 | 0 |
| 1 | 34.4 | 34.4 | 29.5 | 0 | 1.7 |
| 2 | 34.0 | 34.0 | 29.0 | 0 | 3.0 |

Examples 1–2 and Comparative Examples C1–C4 were tested for absorbency in deionized water using the Deionized Water Absorbency Test. Table 2 contains the room temperature density (grams per cubic centimeter) and deionized water absorbency data.

TABLE 2

| Example No. | Density (g/cc) | 1 Hour Water Absorb. Ratio | 2 Hour Water Absorb. Ratio | 4 Hour Water Absorb. Ratio | 6 Hour Water Absorb. Ratio | 24 Hour Water Absorb. Ratio |
|---|---|---|---|---|---|---|
| C1 | 1.1 | 8.7 | 13 | 18 | 20 | 25 |
| C2 | 1.0 | 8.0 | 14 | 21 | 24 | 30 |
| C3 | 1.0 | 8.5 | 14 | 21 | 24 | 28 |
| C4 | 1.0 | 8.3 | 13 | 20 | 24 | 30 |
| 1 | 0.6 | 27 | 33 | 33 | 33 | 38 |
| 2 | 0.5 | 33 | 34 | 34 | 31 | 36 |

The results in Table 2 demonstrate that the un-foamed example (Comparative Example C1) and the examples foamed with a chemical foaming agent (Comparative Examples C2–C4) have substantially lower initial deionized water absorbency than the examples foamed with an expandable microsphere foaming agent (Examples 1–2). The examples foamed with the expandable microsphere foaming agent also maintained void volume upon extrusion as evidenced by a measured room temperature density less than 1.0 gram per cubic centimeter (g/cc). It should be noted that Comparative Examples C2–C4 were foamed upon exiting the extrusion die but lost void volume during the extrusion forming step.

Example 3 and Comparative Example C5

Example 3 and Comparative Example C5 were prepared in the same manner as Examples 1–2 and Comparative Examples C1–C4 except for the following modifications. A mixture of SALCARE SC95 emulsion and silver nitrate solution was prepared by blending a 50 wt-% silver nitrate in deionized water solution into the emulsion using a Ross mixer. The resulting mixture consisted of 98/1/1 SALCARE SC95/silver nitrate/deionized water, all in weight percentages. KRATON D1107P was gravimetrically fed into the feed throat (barrel 1) of the TSE. A mixture of ESCOREZ 1310LC and IRGANOX 1010 was melted at 350° F. (177° C.) and injected into barrel 4. SALCARE SC95/silver nitrate/deionized water mixture was injected at room temperature into barrel 5. MICROPEARL F100D was gravimetrically fed into barrel 7 in the same manner as Examples 1–2. The temperatures of the twin-screw extruder (TSE) were maintained at full cooling, 300° F. (149° C.), 400° F. (204° C.), 300° F. (149° C.), 240° F. (116° C.), 225° F. (107° C.), 225° F. (107° C.), 250° F. (121° C.) and 300° F. (149° C.) for barrels 1 through 9, respectively. The TSE was controlled at 200 revolutions per minute (rpm). The total material throughputs were 151.3 grams per minute and 155.9 grams per minute for Comparative Example C5 and Example 3, respectively. The film die gap was set to 0.015 inch (0.25 mm) for Comparative Example C5 and 0.060 inch (1.0 mm) for Example 3. The compositions were extruded into 2 paper release liners that were contacted to two polished and chromed steel rolls that were maintained at 40° F. (4° C.) at 0.015 inch (0.25 mm) gap for Comparative Example C5 and 0.060 inch (1.5 mm) gap for Example 3. The chilled rolls were set at 3 feet (0.9 meter) per minute take-away speed to provide 0.015 inch (0.25 mm) or 0.060 inch (1.5 mm) thick films for Comparative Example C5 and Example 3, respectively. The un-foamed Comparative Example C5 had an approximate density of 1.0 grams/cm$^3$ (g/cc) whereas the foamed Example 3 had an approximate density of 0.6 g/cc. Table 3 contains the compositional information and for Comparative Example C5 and Example 3.

TABLE 3

| Ex. No. | KRATON D1107 (wt-%) | ESCOREZ 1310LC (wt-%) | SALCARE SC95 (wt-%) | MICROPEARL F100D (wt-%) | Irg. 1010 (wt-%) | DI Water (wt-%) | AgNO$_3$ (wt-%) |
|---|---|---|---|---|---|---|---|
| C5 | 25.0 | 24.0 | 49.0 | 0.0 | 1.0 | 0.50 | 0.50 |
| 3 | 24.3 | 23.3 | 47.6 | 2.9 | 0.97 | 0.49 | 0.49 |

Example 3 and Comparative Example C5 were tested for absorbency in deionized water using the Deionized Water Absorbency Test. Table 4 contains the deionized water absorbency data.

TABLE 4

| Ex. No. | 0.5 Hour Water Absorb. Ratio | 1 Hour Water Absorb. Ratio | 2 Hour Water Absorb. Ratio | 4 Hour Water Absorb. Ratio | 6 Hour Water Absorb. Ratio | 24 Hour Water Absorb Ratio |
|---|---|---|---|---|---|---|
| C5 | 2.6 | 5.9 | 13 | 28 | 37 | 59 |
| 3 | 2.9 | 6.3 | 18 | 41 | 47 | 58 |

Figure 1:
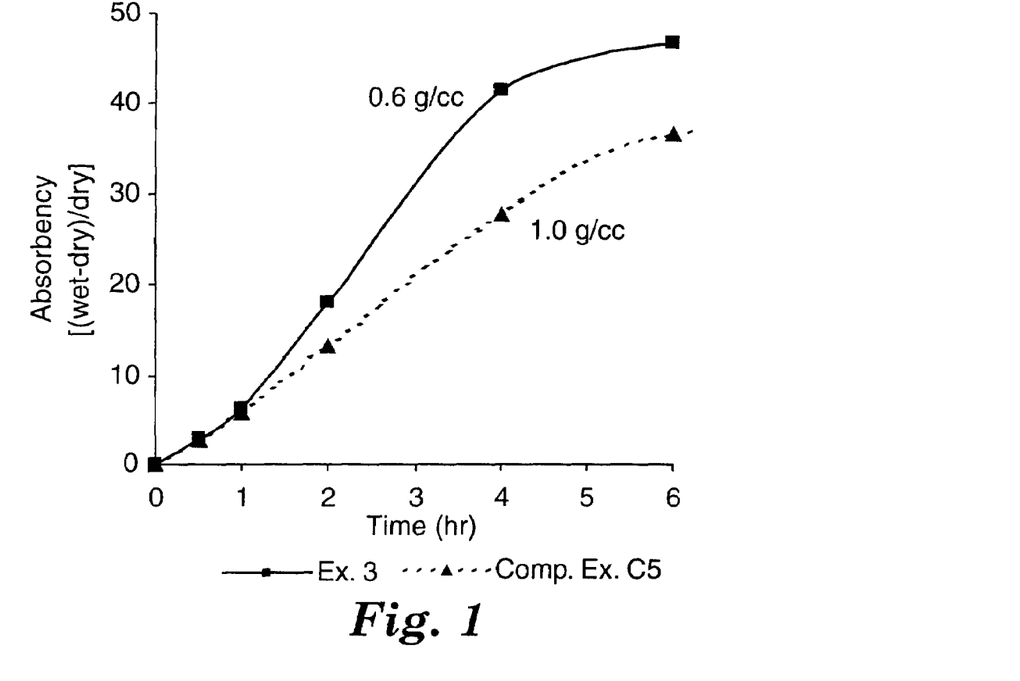
FIG. 1 is a graphical representation of absorbency versus time for Example 3 and Comparative Example C5.

The results in Table 4 demonstrate that the un-foamed example (Comparative Example C5) has substantially lower initial deionized water absorbency than the example foamed with an expandable microsphere foaming agent (Example 3). This result is graphically depicted in FIG. 1.

Example 3 and Comparative Example C5 were also evaluated for anti-microbial activity against Staphylococcus aureus using the 2 Hour % Live Bacteria test. All solution volumes were 7 milliliters. The results are summarized in Table 5.

TABLE 5

| Example No. | Sample Weight (grams) | Calc. AgNO$_3$ Weight (μg) | Calc. Ag+ Weight (μg) | Initial Live Bacteria Concentration (bacteria/mL) | % Live after 2 hours |
|---|---|---|---|---|---|
| C5 | 0.1247 | 624 | 396 | 1.8 × 10$^8$ | 53.1 |
| 3 | 0.0787 | 394 | 250 | 1.8 × 10$^8$ | 30.4 |

The results in Table 5 demonstrate that the un-foamed example (Comparative Example C5) has lower anti-bacterial activity against Staphylococcus aureus than the example foamed with an expandable microsphere foaming agent (Example 3). It is interesting to note that the ratio of the amount of bacteria killed at two hours of the foamed Example 3 to the un-foamed Comparative Example C5 is 1.5 whereas the ratio of absorbed deionized water at two hours for the same examples is 1.4. It is speculated that the bioactive agent (silver salt) is released upon absorbing the aqueous fluid (deionized water). As a consequence, a higher absorbency would lead to a relatively higher amount of active agent released. A high initial bacterial kill is desirable for wound dressings and wound packing materials.

Examples 4–5 and Comparative Examples C6–C7

Solid elastomeric gels consisting of KRATON G1651 and mineral oil were prepared according to the method described in International Publication No. 97/00163 assigned to 3M Company. The compounding process allows for melting of the elastomer followed by sequential addition of heated mineral oil to allow for faster solubility. Table 6 contains the compositional information of the two lots of elastomeric gel that were used for subsequent re-compounding with other additives.

TABLE 6

| Gel No. | KRATON G4609 (wt-%) | KAYDOL Oil (wt-%) | IRGANOX 1010 (wt-%) | Total KRATON G1651 (wt-%) |
|---|---|---|---|---|
| 1 | 19.2 | 80.3 | 0.5 | 10 |
| 2 | 28.8 | 70.7 | 0.5 | 15 |

It should be noted that KRATON G4609 is a mixture of 52 wt-% KRATON G1651 and 48 wt-% KAYDOL mineral oil. Approximately 80 pounds (36 kg) of each gel were extruded into release coated cardboard boxes. Gels 1 and 2 were further blended with SALCARE SC91 and MICROPEARL F100D using a co-rotating twin-screw extruder.

Comparative Example C6 was prepared in the same manner as for Examples 1–2 and Comparative Examples C1–C4 except for the following modifications. Gel No.1 was re-melted and pumped with a BONNOT feeder operating at 25° C. at 90.8 grams per minute (gpm) feed rate into barrel 1 of the TSE. SALCARE SC91 inverse-emulsion polymer was injected at 100° F. (38° C.) and 60.5 gpm feed rate into barrel 5 using a Zenith gear pump. The temperatures of the TSE were maintained at full cooling, 200° F. (93° C.), 200° F. (93° C.), 250° F. (121° C.), 250° F. (121° C.), 250° F. (121° C.), 280° F. (138° C.) and 300° F. (149° C.) for barrels 1 through 9, respectively. The TSE controlled at 300 revolutions per minute (rpm). The TSE was discharged using a Zenith gear pump into 6 inch (15.24 centimeter (cm)) wide single-orifice film die using a conveying hose. The hose, pump and die were all maintained at 300° F. (149° C.). The total material throughput of the extruder was 151.33 gram per minute. The film die gap was set to 0.040 inch (1.0 mm). The chilled rolls were set at 3 feet (0.9 meter) per minute take-away speed to provide 0.060 inch (1.5 mm) thick film. Example 4 was prepared in the same manner as Comparative Example C6 except that MICROPEARL F100D was gravimetrically fed into barrel 7 at 4.5 grams per minute flow rate using an auxiliary single-screw conveying device. The TSE temperature profile was controlled so that the foaming agent would not start expanding until the end of the TSE. Continued expansion was facilitated in both the conveying hose and film die. The foamed composition of Example 4 was extruded into 2 paper release liners that were contacted to two polished and chromed steel rolls that were maintained at 40° F. (4° C.) and 0.060 inches (1.5 mm) gap. Comparative Example C7 and Example 5 were prepared in the same manner as Comparative Example C6 and Example 4 except that (1) Gel No.2 was used instead of Gel No. 1 and (2) the BONNOT was operated at 200° F. (93° C.). Table 7 contains the compositional information for Examples 4–5 and Comparative Examples C6–C7.

TABLE 7

| Ex. No. | KRATON G1651 (wt-%) | SALCARE SC91 (wt-%) | IRGANOX 1010 (wt-%) | MICROPEARL F100D (wt-%) | Ave. Thickness (mm) |
|---|---|---|---|---|---|
| C6 | 6 | 40 | 0.3 | 0 | 1.4 |
| 4 | 5.8 | 38.8 | 0.3 | 3 | 1.4 |
| C7 | 9 | 40 | 0.3 | 0 | 1.7 |
| 5 | 8.7 | 38.8 | 0.3 | 3 | 1.3 |

Examples 4–5 and Comparative Examples C6–C7 were analyzed for their time-dependent absorbency of deionized water over 24 hours using the Deionized Water Absorbancy Test. The 22° C. density and absorbency data for Examples 4–5 and Comparative Examples C6–C7 are presented in Table 8.

TABLE 8

| Example No. | 22° C. Density (g/cc) | 0.5 Hour Water Absorb. Ratio | 1 Hour Water Absorb. Ratio | 2 Hour Water Absorb. Ratio | 6 Hour Water Absorb. Ratio | 24 Hour Water Absorb. Ratio |
|---|---|---|---|---|---|---|
| C6 | 1.1 | 5.8 | 12 | 23 | 40 | 49 |
| 4 | 0.8 | 5.2 | 12 | 26 | 48 | 50 |
| C7 | 1.0 | 3.2 | 7.2 | 15 | 33 | 38 |
| 5 | 0.5 | 3.7 | 9.0 | 37 | 46 | 37 |

Figure 2:
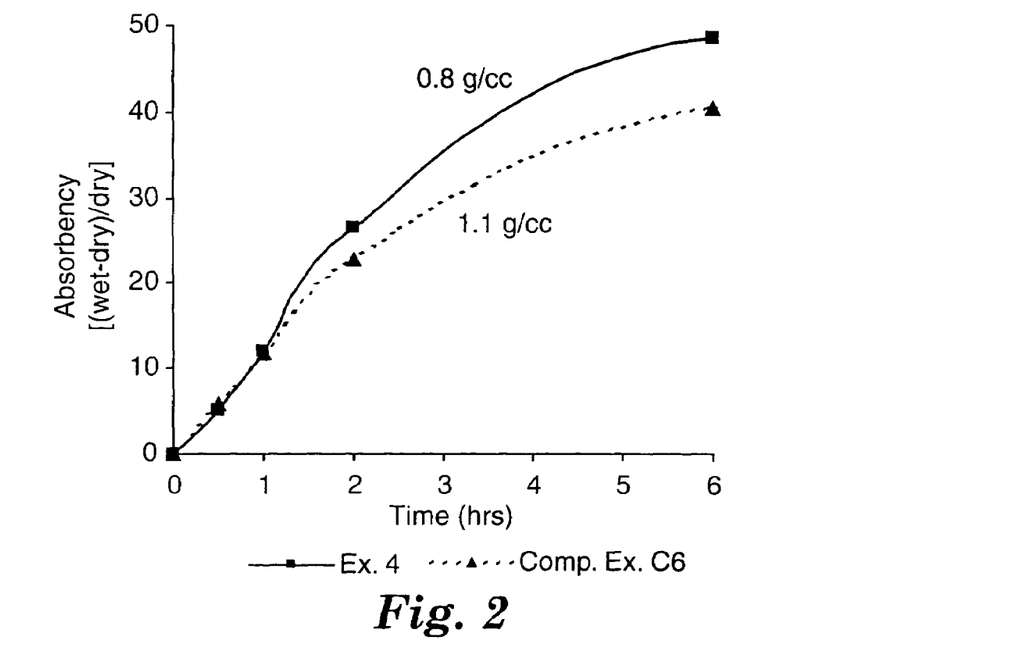
FIG. 2 is a graphical representation of absorbency versus time for Example 4 and Comparative Example C6.
Figure 3:
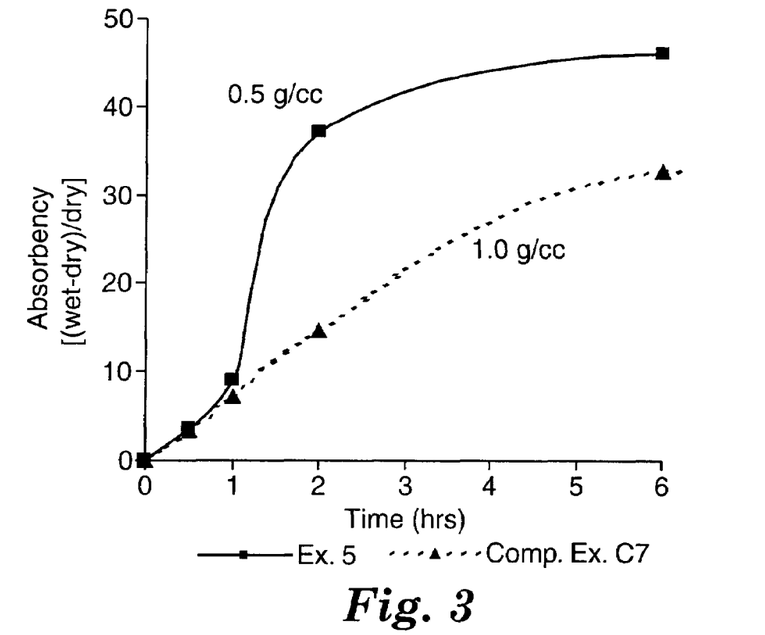
FIG. 3 is a graphical representation of absorbency versus time for Example 5 and Comparative Example C7.

The results in Table 8 demonstrate that the un-foamed examples (Comparative Examples C6–C7) had lower initial absorbance of deionized water compared to their counterparts foamed with expandable microspheres (Examples 4–5). As the density was decreased (Example 4 versus Example 5) the difference in initial absorbency became more significant. These results are graphically depicted in FIGS. 2 and 3.

Examples 6–8

Example 6 was prepared in the same manner as for Example 3 and Comparative Example C5 except for the following modifications. A similar TSE having 12 barrel sections instead of 9 was used to mix the components. KRATON D1107P was gravimetrically fed into the feed throat (barrel 1) of the TSE. A mixture of ESCOREZ 1310LC and IRGANOX 1010 was melted at 350° F. (177° C.) and injected into barrel 3. The previously described 98/1/1 SALCARE SC95/silver nitrate/deionized water mixture (all in weight percentages) was injected at room temperature into barrel 4. MICROPEARL F100D was gravimetrically fed using a KTRON feeder into barrel 9. The temperatures of the twin-screw extruder (TSE) were maintained at 20° C., 204° C., 204° C., 204° C., 204° C., 170° C., 140° C., 115° C., 115° C., 115° C., 115° C. and 115° C. for barrels 1 through 12, respectively. The TSE was controlled at 200 revolutions per minute (rpm). The total material throughputs were 147 grams per minute for Examples 6 and 7. The transport hose, ZENITH gear pump and contacting rotating-rod coating die were all maintained at 120° C. for Example 7 to ensure that the expandable microspheres would not expand during the compounding and coating processes. The transport hose, ZENITH gear pump and contacting rotating-rod coating die were all maintained at 150° C. for Example 6 to ensure that the expandable microspheres expanded during the entire mixing and coating processes. Table 9 contains the compositional information for Example 6 and Example 7.

TABLE 9

| Ex No. | KRATON D1107 (wt-%) | ESCOREZ 1310LC (wt-%) | SALCARE SC95 (wt-%) | MICROPEARL F100D (wt-%) | Irg. 1010 (wt-%) | DI Water (wt-%) | AgNO$_3$ (wt-%) |
|---|---|---|---|---|---|---|---|
| 6 | 24.3 | 23.8 | 47.5 | 2.9 | 0.5 | 0.5 | 0.5 |
| 7 | 24.3 | 23.8 | 47.5 | 2.9 | 0.5 | 0.5 | 0.5 |

To assess the effect of oven foaming versus extrusion foaming Example 7 was placed in a convection oven at 350° F. (177° C.) for 1 minute. The oven-foamed Example 7 was designated as Example 8. Examples 6–8 were analyzed for their time-dependent absorbency of deionized water over 24 hours using the Deionized Water Absorbency Test. The 22° C. density and absorbency for Examples 6–8 data are presented in Table 10.

TABLE 10

| Ex No. | 22° C. Density (g/cc) | 0.5 Hour Water Absorb. Ratio | 1 Hour Water Absorb. Ratio | 2 Hour Water Absorb. Ratio | 4 Hour Water Absorb. Ratio | 6 Hour Water Absorb. Ratio | 24 Hour Water Absorb. Ratio |
|---|---|---|---|---|---|---|---|
| 6 | 0.59 | 19 | 46 | 52 | 54 | 58 | 63 |
| 7 | 0.90 | 15 | 31 | 43 | 49 | 55 | 62 |
| 8 | 0.64 | 6.2 | 20 | 41 | 47 | 51 | 64 |

Figure 4:
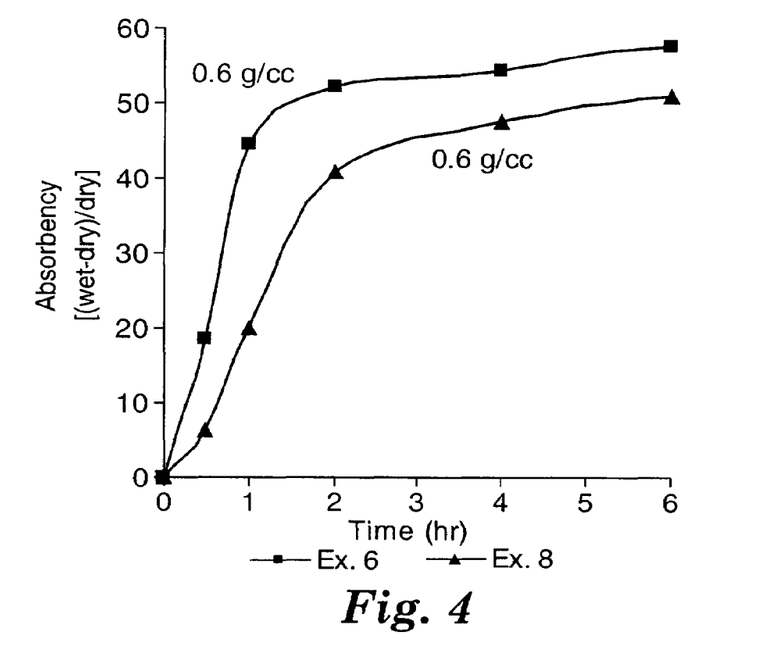
FIG. 4 is a graphical representation of absorbency versus time for Example 6 and Example 8.

The deionized water results presented in Table 10 demonstrate that the extrusion foamed absorbent composition (Example 6) had substantially higher initial absorbency (up to 4 hours dwell time) than both the un-foamed composition (Example 7) and the oven-foamed composition (Example 8). This result is graphically depicted in FIG. 4. It is interesting to note that the extrusion-foamed composition of the invention had substantially higher initial absorbency than the oven-foamed example even though both compositions had similar density and correspondingly similar void space. It is presumed that the relatively higher initial absorbency is a result of absorbing aqueous fluids being able to more readily access the void space in the extrusion-foamed compositions of the invention although the mechanism is not well understood at this time.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. An absorbent polymer composition comprising:
   a polymeric material;
   absorbent particles; and
   thermally expandable microspheres, wherein a thermally expandable microsphere comprises a thermoplastic polymeric shell and a core that includes a liquid and/or gas.

2. The polymer composition of claim 1 wherein the absorbent particles are provided in the form of a hydrocolloid.

3. The polymer composition of claim 1 wherein the absorbent particles are superabsorbent.

4. The polymer composition of claim 1 wherein the polymeric material comprises a pressure sensitive adhesive.

5. The polymer composition of claim 1 wherein the absorbent particles are dispersed in a hydrophobic oil.

6. The polymer composition of claim 5 wherein the absorbeQt particles are provided in an inverse emulsion of crosslinked hydrophilic polymer microparticles dispersed in a hydrophobic oil.

7. The polymer composition of claim 1 wherein the polymeric material comprises a mixture of different polymers.

8. The polymer composition of claim 1 further comprising a bioactive agent.

9. The polymer composition of claim 1 in the form of an extruded article.

10. An absorbent polymer foam composition comprising:
    a polymeric material;
    absorbent particles; and
    thermally expanded microspheres prepared from thermally expandable microspheres, wherein a thermally expandable microsphere comprises a thermoplastic polymeric shell and a core that includes a liquid and/or gas.

11. The polymer foam composition of claim 10 which has a density of less than 0.8 gram per cubic centimeter.

12. The polymer foam composition of claim 10 wherein the absorbent particles are provided in the form of a hydrocolloid.

13. The polymer foam composition of claim 10 wherein the absorbent particles are superabsorbant.

14. The polymer foam composition of claim 10 wherein the polymeric material comprises a pressure sensitive adhesive.

15. The polymer foam composition of claim 10 wherein the absorbent particles are provided in an inverse emulsion of crosslinked hydrophilic polymer microparticles dispersed in a hydrophobic oil.

16. The polymer foam composition of claim 10 wherein the polymeric material comprises a mixture of different polymers.

17. The polymer foam composition of claim 10 further comprising a bioactive agent.

18. An absorbent polymer foam composition comprising:
    a polymeric material;
    a hydrocolloid comprising superabsorbent particles; and
    thermally expanded microspheres prepared from thermally expandable microspheres, wherein a thermally expandable microsphere comprises a thermoplastic polymeric shell and a core that includes a liquid and/or gas;
    wherein the polymer foam has a density of less than 0.8 gram per cubic centimeter.

19. An absorbent polymer foam composition preparable by a method comprising:
    combining a polymeric material, absorbent particles, and thermally expandable microspheres at a temperature below the expansion temperature of the microspheres to form a mixture, wherein a thermally expandable microsphere comprises a thermoplastic polymeric shell and a core that includes a liquid and/or gas; and increasing the temperature of the mixture above the expansion temperature of the thermally expandable microspheres to form an absorbent polymer foam.

20. The absorbent polymer foam composition of claim 19 wherein the polymeric material comprises a pressure sensitive adhesive.

21. The absorbent polymer foam composition of claim 19 wherein the absorbent particles are provided in an inverse emulsion of crosslinked hydrophilic polymer microparticles dispersed in a hydrophobic oil.

22. The absorbent polymer foam composition of claim 19 wherein the polymeric material comprises a mixture of different polymers.

23. The absorbent polymer foam composition of claim 19 further comprising a bioactive agent.

24. A method of making an absorbent polymer foam composition, wherein the method comprises:

combining a polymeric material, absorbent particles; and thermally expandable microspheres to form a mixture in an extruder at a temperature below the expansion temperature of the microspheres, wherein a thermally expandable microsphere comprises a thermoplastic polymeric shell and a core that includes a liquid and/or gas; and increasing the temperature of the mixture above the expansion temperature of the thermally expandable microspheres during extrusion.

25. The method of claim 24 wherein the resultant foamed composition has a density of less than 0.8 gram per cubic centimeter.

26. A medical article comprising the composition of claim 1.

27. The medical article of claim 26 which is a wound dressing or a wound packing material.

28. A medical article comprising the composition of claim 10.

29. The medical articic of claim 28 which is a wound dressing or a wound packing material.

30. A medical article comprising the composition of claim 18.

31. The medical article of claim 30 which is a wound dressing or a wound packing material.

32. A method of using a polymer composition comprising applying the polymer composition of claim 1 to a wound.

33. A method of using a polymer composition comprising applying the polymer composition of claim 10 to a wound.

34. A method of using a polymer composition comprising applying the polymer composition of claim 18 to a wound.

* * * * *

UNITED STATES PATENT AND TRADEMARK OFFICE
CERTIFICATE OF CORRECTION

PATENT NO. : 7,285,576 B2
APPLICATION NO. : 10/387236
DATED : October 23, 2007
INVENTOR(S) : Patrick D. Hyde It is certified that error appears in the above-identified patent and that said Letters Patent is hereby corrected as shown below:

On the Title Page, in Column 1, under (U.S. Patent Documents)
Line 21, delete "Lehr" and insert -- Leir --, therefor.

On Page 2, in Column 2, under (Other Publications)
Line 21, delete "Atricles" and insert -- Articles --, therefor.

Column 2
Line 21, delete ""e.g.," and insert -- (e.g., --, therefor.

Column 4
Line 24, delete "thereof-," and insert -- thereof; --, therefor.
Line 29, delete "polymnethylmethacrylate;" and insert -- polymethylmethacrylate; --, therefor.
Lines 33-34, delete "thermnoplastics" and insert -- thermoplastics --, therefor.
Line 55, delete "HYTR-EL" and insert -- HYTREL --, therefor.

Column 5
Line 28, delete "N-N'di-beta-" and insert -- N-N' di-beta- --, therefor.
Line 33, delete "propianate]" and insert -- propionate] --, therefor.
Line 58, delete "styreneibutadiene" and insert -- styrene/butadiene --, therefor.

Column 7
Line 17, delete "130," and insert -- I30, --, therefor.
Line 18, delete "160," and insert -- I60, --, therefor.
Line 18, delete "160D" and insert -- I60D --, therefor.
Line 19, delete "165D;" and insert -- I65D; --, therefor.

Column 9
Line 46, delete "Absorbant" and insert -- Absorbent --, therefor.

Column 10
Line 33, delete "1 -vinyl-imidazole," and insert -- 1-vinyl-imidazole, --, therefor.

UNITED STATES PATENT AND TRADEMARK OFFICE
CERTIFICATE OF CORRECTION

PATENT NO. : 7,285,576 B2
APPLICATION NO. : 10/387236
DATED : October 23, 2007
INVENTOR(S) : Patrick D. Hyde It is certified that error appears in the above-identified patent and that said Letters Patent is hereby corrected as shown below:

Column 15
Line 33, delete "polyvinylchioride" and insert -- polyvinylchloride --, therefor.

Column 17
Line 10, delete "MiliQ" and insert -- MilliQ --, therefor.
Line 18, delete "milliwatts" and insert -- milliWatts --, therefor.

Column 19
Line 49, after "Absorb" insert -- . --. (Last occurrence)

Column 21
Lines 2-3, delete "C 1-C4" and insert -- C1-C4 --, therefor.
Line 11, after "(121° C.)," insert -- 250° F. (121° C.), --.
Line 12, after "TSE" insert -- was --.
Line 53, delete "Absorbancy" and insert -- Absorbency --, therefor.

Columns 21-22
Line 60, delete "ESCROREZ" and insert -- ESCOREZ --, therefor.

Column 23
Line 54, in Claim 1, delete "cxpandable" and insert -- expandable --, therefor.

UNITED STATES PATENT AND TRADEMARK OFFICE
CERTIFICATE OF CORRECTION

PATENT NO. : 7,285,576 B2
APPLICATION NO. : 10/387236
DATED : October 23, 2007
INVENTOR(S) : Patrick D. Hyde

It is certified that error appears in the above-identified patent and that said Letters Patent is hereby corrected as shown below:

<u>Column 24</u>
Line 2, in Claim 6, delete "absorbeQt" and insert -- absorbent --, therefor.
Line 36, in Claim 12, delete "particlcs" and insert -- particles --, therefor.
Line 39, in Claim 13, delete "superabsorbant." and insert -- superabsorbent. --, therefor.

<u>Column 26</u>
Line 13, in Claim 29, delete "articic" and insert -- article --, therefor.

Signed and Sealed this

Third Day of June, 2008

JON W. DUDAS
*Director of the United States Patent and Trademark Office*